United States Patent
Chen et al.

(10) Patent No.: US 11,440,866 B2
(45) Date of Patent: Sep. 13, 2022

(54) SYSTEMS AND METHODS FOR PURIFYING SOLVENTS

(71) Applicant: Fujifilm Electronic Materials U.S.A., Inc., N. Kingstown, RI (US)

(72) Inventors: Yuan Chen, Chandler, AZ (US); Eduardo Ramirez Romero, Grapevine, TX (US); Bryan Hinzie, Gilbert, AZ (US)

(73) Assignee: Fujifilm Electronic Materials U.S.A., Inc., N. Kingstown, RI (US)

( * ) Notice: Subject to any disclaimer, the term of this patent is extended or adjusted under 35 U.S.C. 154(b) by 0 days.

(21) Appl. No.: 17/342,581

(22) Filed: Jun. 9, 2021

(65) Prior Publication Data

US 2021/0387937 A1    Dec. 16, 2021

Related U.S. Application Data

(60) Provisional application No. 63/038,463, filed on Jun. 12, 2020.

(51) Int. Cl.
| | |
|---|---|
| *C07C 45/82* | (2006.01) |
| *B01D 3/00* | (2006.01) |
| *C07C 45/78* | (2006.01) |
| *B01D 3/14* | (2006.01) |
| *B01D 39/16* | (2006.01) |
| *B01D 36/00* | (2006.01) |
| *C11D 11/00* | (2006.01) |
| *B01J 20/26* | (2006.01) |
| *C11D 7/50* | (2006.01) |

(52) U.S. Cl.
CPC ............ *C07C 45/783* (2013.01); *B01D 3/143* (2013.01); *B01D 36/00* (2013.01); *B01D 39/16* (2013.01); *B01J 20/261* (2013.01); *C11D 7/5022* (2013.01); *C11D 11/0047* (2013.01)

(58) Field of Classification Search
CPC ................................ C07C 45/82; B01D 3/143
See application file for complete search history.

(56) References Cited

U.S. PATENT DOCUMENTS

| | | |
|---|---|---|
| 3,149,166 A | 9/1964 | Poehler et al. |
| 4,306,944 A | 12/1981 | Murthy et al. |
| 6,982,026 B2 | 1/2006 | Cockrem et al. |
| 7,867,365 B2 | 1/2011 | Brown |
| 7,931,784 B2 | 4/2011 | Medoff |
| 8,062,706 B2 | 11/2011 | Lozano |
| 2008/0011597 A1 | 1/2008 | Spani |
| 2019/0258168 A1 | 8/2019 | Kamimura et al. |

FOREIGN PATENT DOCUMENTS

| | | | |
|---|---|---|---|
| JP | 2004-10530 | 1/2004 | ............. C07C 67/54 |
| JP | 2010-163539 | 7/2010 | ............. C10G 75/04 |
| JP | 2016-73922 | 5/2016 | ............. B01D 61/14 |
| WO | WO 2018/084302 | 5/2018 | ............... G03F 7/26 |

OTHER PUBLICATIONS

International Search Report and Written Opinion of the International Searching Authority for International Application No. PCT/US2021/036552, dated Sep. 16, 2021.

*Primary Examiner* — Sikarl A Witherspoon
(74) *Attorney, Agent, or Firm* — Fish & Richardson P.C.

(57) ABSTRACT

The present disclosure is directed to methods and systems of purifying solvents. The purified solvents can be used, e.g., as pre-wet liquids, solution developers, and cleaners in a multistep semiconductor manufacturing process.

33 Claims, 1 Drawing Sheet

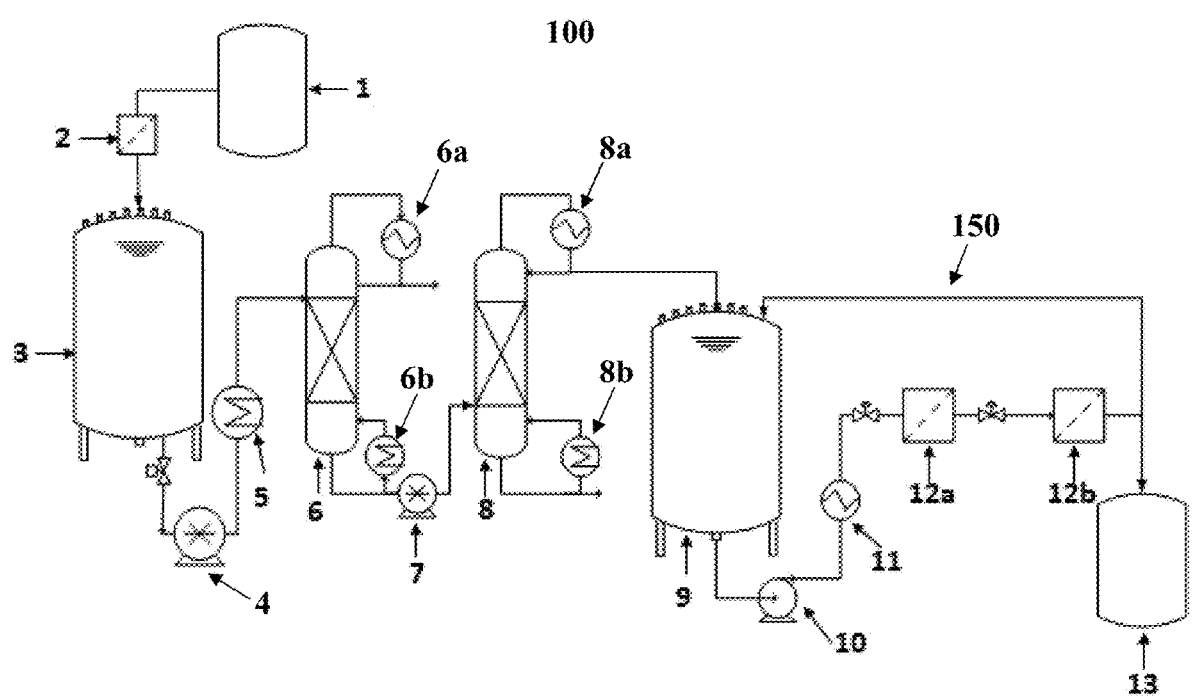

SYSTEMS AND METHODS FOR PURIFYING SOLVENTS

CROSS-REFERENCE TO RELATED APPLICATION

The present application claims priority to U.S. Provisional Application Ser. No. 63/038,463, filed on Jun. 12, 2020, the contents of which are hereby incorporated by reference in their entirety.

FIELD OF THE DISCLOSURE

The present disclosure relates to systems and methods for purifying solvents (e.g., organic solvents). In particular, the present disclosure relates to systems and methods that can be used to obtain organic solvents having a high purity, a low on wafer particle count, and a low on wafer metal count.

BACKGROUND OF THE DISCLOSURE

The semiconductor industry has achieved rapid improvements in integration density of electronic components, which are arisen from continuous reductions in the component size. Ultimately, more of the smaller components are afforded to be integrated into a given area. These improvements are mostly due to the development of new precision and high resolution processing techniques.

During the manufacturing of high resolution integrated circuits (ICs), various processing liquids will come into contact with a bare wafer or a film-coated wafer. For example, the fabrication of a fine metal interconnection typically involves a procedure of coating a base material followed by a pre-wetting liquid before the base material is coated with a composite liquid to form a resist film. These processing liquids, containing proprietary ingredients and various additives, are known to be a source of contamination of IC wafer.

It is believed that even if a trace amount of contaminants is mixed into these chemical liquids, such as a wafer pre-wetting liquid or a developer solution, the resulting circuit patterns may have defects. For example, it is known that the presence of very low levels of metal impurities may interfere with the performance and stability of semiconductor devices. Depending on the kind of metallic contaminants, oxide property can deteriorate, inaccurate patterns can be formed, electrical performance of semiconductor circuits can be impaired, which eventually adversely impact manufacturing yields.

The contamination of impurities, such as metal impurities, fine particles, organic impurities, moisture, and the like, can be inadvertently introduced in a chemical liquid during various stages of the manufacturing of the chemical liquid. Examples include impurities that are presented in a raw material, a by-product generated or an unreacted reactant remained when the chemical liquid is manufactured, or foreign matters eluded or extracted from the surface of the manufacturing apparatus or from a container equipment, reaction vessels, or the like used in transporting, storing or reacting. Hence, a reduction or removal of insoluble and soluble contaminants from these chemical liquids used for the production of highly precise and ultra-fine semiconductor electronic circuits is a basic assurance of producing defective-free ICs.

In this respect, it is imperative to significantly improve and to rigorously control the standard and quality of chemical liquid manufacturing processes and systems in order to form high purity chemical liquids, which are indispensable in the fabrication of ultra-fine and immensely precise semiconductor electronic circuits.

SUMMARY OF THE DISCLOSURE

Accordingly, to form highly precise integrated circuits, the demands for ultra-pure chemical liquids, and the quality improvement and control of theses liquids become very critical. Specific key parameters targeted for quality improvement and control include: liquid and on-wafer metal reduction, liquid and on-wafer particle count reduction, on-wafer defect reduction, and organic contaminant reduction.

In view of the above, the present disclosure provides purification systems and methods of purifying a solvent (e.g., an organic solvent) using the same for preparing a solvent targeted for semiconductor manufacturing, in which an ultra-pure solvent is produced with the amounts of particles, metallic impurities, organic impurities, and residual moisture in the solvent managed within predetermined ranges and without the generation or introduction of unknown and unwanted substances. Hence, the occurrence of residue and/or particle defects is suppressed and the yield of semiconductor wafer is improved. In addition, the inventor found unexpectedly that purifying an organic solvent by using both a first distillation column having an inlet positioned at a location that is from about 80% to about 100% of the height of the first distillation column to remove low boiling organic impurities and a second distillation column having an inlet positioned at a location that is from about 0% to about 30% of the height of the second distillation column to remove high boiling organic impurities can significantly increase energy efficiency and reduce the on-wafer metal counts and on-wafer particle counts when the purified organic solvent is used to treat a wafer. Further, the inventor found unexpectedly that preheating an organic solvent at a temperature at most about 20° C. below the boiling point of the organic solvent before distilling the organic solvent can also significantly improve the efficiency of the purification methods scribed herein, reduce the energy needed to distill the solvent, and reduce the purification cost.

In one aspect, the disclosure features a method (e.g., a continuous method) of purifying an organic solvent that includes (1) distilling the organic solvent in a first distillation column to obtain an intermediate organic solvent, (2) transferring the intermediate organic solvent to a second distillation column, and (3) distilling the intermediate organic solvent in the second distillation column to obtain a distilled organic solvent. The first distillation column has an inlet positioned at a location that is from about 80% to about 100% of the height of the first distillation column (e.g., to remove the low boiling organic impurities). The second distillation column has an inlet positioned at a location that is from about 0% to about 30% of the height of the second distillation column (e.g., to remove high boiling organic impurities).

In another aspect, the disclosure features a system that includes (1) a first distillation column having a first inlet and a first outlet, and (2) a second distillation column downstream of the first distillation column and having a second inlet and a second outlet. The first inlet is positioned at a location that is from about 80% to about 100% of the height of the first distillation column (e.g., to remove low boiling organic impurities). The second inlet is in fluid communication with the first outlet, and the second inlet is positioned at a location that is from about 0% to about 30% of the height of the second distillation column (e.g., to remove high boiling organic impurities).

Embodiments can include one or more of the following features.

In some embodiments, distilling the organic solvent in the first distillation column removes impurities having a boiling point lower than the boiling point of the organic solvent. In some embodiments, distilling the intermediate organic solvent in the second distillation column removes impurities having a boiling point higher than the boiling point of the organic solvent.

In some embodiments, the method further includes preheating the organic solvent to a temperature at least about 20° C. below the boiling point of the organic solvent before distilling the organic solvent in the first distillation column, in which the preheating is performed by a preheater upstream of and in fluid communication with the first distillation column.

In some embodiments, the method further includes passing the organic solvent through a first filter unit upstream of the first distillation column, in which the first filter unit includes a first housing and at least one first filter in the first housing, and the at least one first filter includes a filtration medium. In some embodiments, the filtration medium in the at least one first filter includes a polyolefin (e.g., polypropylene), a polyamide (e.g., a nylon), a fluoropolymer (e.g., a polytetrafluoroethylene), or a copolymer thereof. In some embodiments, the filtration medium in the at least one first filter has an average pore size from about 50 nm to about 250 nm. In some embodiments, the at least one first filter is a particle removal filter.

In some embodiments, the method further includes passing the distilled organic solvent through a second filter unit downstream of the second distillation column, in which the second filter unit includes a second housing and at least one second filter in the second housing, and the at least one second filter includes a filtration medium. In some embodiments, the filtration medium in the at least one second filter includes a polyolefin (e.g., polypropylene), a polyamide (e.g., a nylon), a fluoropolymer (e.g., a polytetrafluoroethylene), or a copolymer thereof. In some embodiments, the filtration medium in the at least one second filter has an average pore size from about 2 nm to 10 nm. In some embodiments, the at least one second filter is a particle removal filter.

In some embodiments, the method further includes recirculating the organic solvent exiting the second filter unit. In some embodiments, the recirculating includes moving the organic solvent exiting the second filter unit to a distilled solvent tank and subsequently passing the organic solvent through the second filter unit, and the distilled solvent tank is between and in fluid communication with the second distillation column and the second filter unit.

In some embodiments, the method further includes moving the distilled organic solvent to a product container downstream of and in fluid communication with the second distillation column.

In some embodiments, the organic solvent includes cyclohexanone, ethyl lactate, n-butyl acetate, propylene glycol monomethyl ether, propylene glycol monomethyl ether acetate, 4-methyl-2-pentanol, or propylene carbonate.

In some embodiments, the system further includes a preheater, wherein the preheater is upstream of and in fluid communication with the first distillation column.

In some embodiments, the system further includes a first filter unit upstream of and in fluid communication with the preheater, in which the first filter unit includes a first housing and at least one first filter in the first housing, and the at least one first filter comprises a includes medium.

In some embodiments, the system further includes a second filter unit downstream of the second distillation column, in which the second filter unit includes a second housing and at least one second filter in the second housing, and the at least one second filter includes a filtration medium.

In some embodiments, the system further includes a distilled solvent tank between and in fluid communication with the second distillation column and the second filter unit.

In some embodiments, the system further includes a recirculation loop, in which the recirculation loop includes the second filter unit and the distilled solvent tank.

In some embodiments, the system further includes a product container downstream of and in fluid communication with the second distillation column.

BRIEF DESCRIPTION OF THE DRAWING

FIG. 1 is a schematic diagram showing an example of a purification system adopted in a method of purifying an organic solvent in accordance with some embodiments of the present disclosure.

DETAILED DESCRIPTION OF THE DISCLOSURE

As defined herein, unless otherwise noted, all percentages expressed should be understood to be percentages by weight to the total weight of a composition. Unless otherwise noted, ambient temperature is defined to be between about 16 and about 27 degrees Celsius (° C.). The term "solvent" mentioned herein, unless otherwise noted, refers to a single solvent or a combination of two or more (e.g., three or four) solvents. In the present disclosure, "ppm" means "parts-per-million", "ppb" means "parts-per-billion" and "ppt" means "parts-per-trillion", based on the total weight of a composition.

In general, the disclosure features systems and methods for purifying a solvent (e.g., an organic solvent). The solvent mentioned herein can be used in a wafer processing solution (such as a pre-wetting liquid, a developer solution, a rinsing solution, a cleaning solution, or a stripping solution), or a solvent for a semiconductor material used in any semiconductor manufacturing process.

Prior to being subjected to a purification method of the present disclosure, a solvent may contain an undesirable amount of contaminants and impurities (such as organic impurities, metal impurities, particles, and moisture). After the solvent is processed by the purification method of the present disclosure, substantial amounts of the contaminants and impurities can be removed from the solvent. A pre-processed solvent is also referred to in the present disclosure as an "unpurified solvent". The pre-processed solvent can be synthesized in house or commercially available via purchasing from a supplier. A post-processed solvent is also referred to in the present disclosure as a "purified solvent". A "purified solvent" can include impurities limited within predetermined ranges.

In general, the solvent mentioned herein can include at least one (e.g., two, three, or four) organic solvent, such as an alcohol, an ether, a hydrocarbon, a halogenated hydrocarbon, an ester, a ketone, or a carbonate. Examples of suitable organic solvents include methanol, ethanol, 1-propanol, isopropanol, n-propanol, 2-methyl-1-propanol, n-butanol, 2-butanol, tert-butanol, 1-pentanol, 2-pentanol, 3-pentanol, n-hexanol, cyclohexanol, 2-methyl-2-butanol, 3-methyl-2-butanol, 2-methyl-1-butanol, 3-methyl-1-butanol, 2-methyl-1-pentanol, 2-methyl-2-pentanol, 2-methyl-3-pentanol, 3-methyl-1-pentanol, 3-methyl-2-pentanol, 3-methyl-3-pentanol, 4-methyl-1-pentanol, 4-methyl-2-pentanol, 2-ethyl-1-butanol, 2,2-dimethyl-3-pentanol, 2,3-dimethyl-3-pentanol, 2,4-dimethyl-3-pentanol, 4,4-dimethyl-2-pentanol, 3-ethyl-3-heptanol, 1-heptanol, 2-heptanol, 3-heptanol, 2-methyl-2-hexanol, 2-methyl-3-hexanol, 5-methyl-1-hexanol, 5-methyl-2-hexanol, 2-ethyl-1-hexanol, methylcyclohexanol, trimethylcyclohexanol, 4-methyl-3-heptanol, 6-methyl-2-heptanol, 1-octanol, 2-octanol, 3-octanol, 2-propyl-1-pentanol, 2,6-dimethyl-4-heptanol, 2-nonanol, 3,7-dimethyl-3-octanol, ethylene glycol, propylene glycol, diethyl ether, dipropyl ether, diisopropyl ether, butyl methyl ether, butyl ethyl ether, butyl propyl ether, dibutyl ether, diisobutyl ether, tert-butyl methyl ether, tert-butyl ethyl ether, tert-butyl propyl ether, di-tert-butyl ether, dipentyl ether, diisoamyl ether, cyclopentyl methyl ether, cyclohexyl methyl ether, Zo bromomethyl methyl ether, α,α-dichloromethyl methyl ether, chloromethyl ethyl ether, 2-chloroethyl methyl ether, 2-bromoethyl methyl ether, 2,2-dichloroethyl methyl ether, 2-chloroethyl ethyl ether, 2-bromoethyl ethyl ether, (±)-1,2-dichloroethyl ethyl ether, 2,2,2-trifluoroethyl ether, ethyl vinyl ether, butyl vinyl ether, allyl ethyl ether, allyl propyl ether, allyl butyl ether, diallyl ether, 2-methoxypropene, ethyl-1-propenyl ether, cis-1-bromo-2-ethoxyethylene, 2-chloroethyl vinyl ether, allyl-1,1,2,2-tetrafluoroethyl ether, octane, isooctane, nonane, decane, methylcyclohexane, decalin, xylene, ethylbenzene, diethylbenzene, cumene, sec-butylbenzene, cymene, dipentene, methyl pyruvate, monomethyl ether, propylene glycol monomethyl ether, propylene glycol monoethyl ether, propylene glycol monopropyl ether, propylene glycol monomethyl ether acetate, ethyl lactate, methyl methoxypropionate, cyclopentanone, cyclohexanone, n-butyl acetate, γ-butyrolactone, diisoamyl ether, isoamyl acetate, chloroform, dichloromethane, 1,4-dioxane, hexyl alcohol, 2-heptanone, isoamyl acetate, propylene carbonate, and tetrahydrofuran.

In some embodiments, the solvent is a pre-wetting liquid. Examples of a pre-wetting liquid include at least one of cyclopentanone (CyPe), cyclohexanone (CyH), monomethyl ether, propylene glycol monomethyl ether (PGME), propylene glycol monoethyl ether (PGEE), propylene glycol monomethyl ether acetate (PGMEA), propylene glycol monopropyl ether (PGPE), and ethyl lactate (EL). In some embodiments, the solvent can be a developer solution such as n-butyl acetate, or a rinsing liquid such as 4-methyl-2-pentanol (MIBC). In some embodiments, the solvent can be a rinse solvent used in a wafer manufacturing process, such as isopropyl alcohol.

In some embodiments, the pre-processed or unpurified organic solvent can have a purity of at most about 99.95% (e.g., at most about 99.5%, at most about 99%, at most about 98%, at most about 97%, at most about 96%, or at most about 95%). In some embodiments, the post-processed or purified organic solvent obtained from the methods described herein can have a purity of at least about 99.99% (e.g., at least at least about 99.995%, at least about 99.999%, at least about 99.9995%, at least about 99.9999%, or 100%). As mentioned herein, "purity" refers to the weight percentage of the solvent in the total weight of the liquid. The content of the organic solvent in a liquid can be measured by using a gas chromatography mass spectrometry (GC-MS) device (e.g., a thermal desorption (TD) GC-MS device).

In some embodiments, the boiling point of the solvent described herein is at most about 200° C. (e.g., at most about 175° C. or at most about 150° C.) or at least about 50° C. (e.g., at least about 75° C. or at least about 100° C.) from a point of improving manufacturing yield of a semiconductor chip. For example, when the solvent is cyclohexanone, its boiling point is about 155.6° C. In this disclosure, the boiling point means a boiling point measured at 1 atm.

In general, impurities contained in a pre-processed organic solvent can include metallic impurities, particles, and others such as organic impurities and moisture.

As described herein, metal impurities can be in a form of a solid (e.g., metal simplex, particulate metal-containing compound, and the like). In some embodiments, metal impurities can include a metal selected from the group consisting of alkali metals, alkaline earth metals, main group metals, transition metals, and lanthanide metals. Examples of common metallic impurities include heavy metals such as copper (Cu), iron (Fe), aluminum (Al), chromium (Cr), lead (Pb), nickel (Ni), zinc (Zn), and lead (Pb); and alkali or alkaline earth metals such as sodium (Na), potassium (K), and calcium (Ca). Depending on the type of metal, metal impurities can deteriorate oxide integrity, degrade MOS gate stacks, and reduce lifetime of devices. In some embodiments, the content of each metal component in the pre-processed solvent ranges from about 0.1 to about 2000 ppt (e.g., from about 200 to about 1000 ppt or from about 500 to about 1000 ppt).

In an organic solvent purified by the methods described herein, the total trace metal content is preferred to be within a predetermined range of from 0 (e.g., at least about 1 ppt, at least about 5 ppt, or at least about 10 ppt) to at most about 200 ppt (e.g., at most about 180 ppt, at most about 160 ppt, at most about 150 ppt, at most about 140 ppt, at most about 120 ppt, at most about 100 ppt, at most about 50 ppt, or at most about 20 ppt) in mass, and the amount of each trace metal (e.g., Fe, Ni, Cr, Zn, Cu, K, Na, or Ca) is preferred to be within a predetermined range of from 0 (e.g., at least about 1 ppt, at least about 2 ppt, or at least about 3 ppt) to at most about 20 ppt (at most about 15 ppt, at most about 10 ppt, at most about 8 ppt, at most about 6 ppt, at most about 5 ppt, at most about 4 ppt, at most about 3 ppt, or at most about 2 ppt) in mass.

In the present disclosure, substances having a size of 0.03 μm or greater are referred to as "particles" or "particulates". Examples of particles include dust, dirt, organic solid matters, and inorganic solid matters. The particles can also include impurities of colloidalized metal atoms. The type of the metal atoms that are easily colloidalized is not particularly limited, and can include at least one metal atom selected from the group consisting of Na, K, Ca, Fe, Cu, Mg, Mn, Li, Al, Cr, Ni, Zn, and Pb. In an organic solvent purified by the methods described herein, the total number of the particles having a size of 0.03 μm or more (e.g., 0.05 μm or more) is preferred to be within a predetermined range of at most about 50 (at most about 40, at most about 20, at most about 10, at most about 5, at most about 1, or 0) per 1 ml of the solvent. The number of "particles" in a liquid medium can be counted by a light scattering type in-liquid particle counter and is referred as LPC (liquid particle count).

As described herein, organic impurities are different from the organic solvent and refer to organic matters that are contained in the content of 5000 mass ppm or smaller with respect to the total mass of the liquid containing the organic solvent and the organic impurities. Organic impurities can be volatile organic compounds that are present in ambient air even inside a clean-room. Some of the organic impurities originate from shipping and storage equipment, while some are presented in a raw material from the start. Other examples of organic impurities include a by-product generated when the organic solvent is synthesized and/or an unreacted reactant. Examples of organic impurities include aliphatic hydrocarbons (e.g., $C_8$-$C_{24}$ alkanes or alkenes having 8 or more carbons), aromatic hydrocarbons, ethers, esters, and aldehydes.

The total content of the organic impurities in a purified organic solvent is not particularly limited. From a point of improving the manufacturing yield of a semiconductor device, the total content of the organic impurities can be at most about 500 ppm (e.g., at most about 400 ppm, at most about 300 ppm, at most about 200 ppm, at most about 100 ppm, at most about 50 ppm, at most about 20 ppm, at most about 10 ppm) and/or at least about 1 ppm (at least about 10 ppm or at least about 100 ppm) of the purified organic solvent. In some embodiments, the purified organic solvent has a trace amount (e.g., at most about 1 ppm) of any measurable organic impurities. The content of the organic impurities in the solvent described herein can be measured by using a gas chromatography mass spectrometry (GC-MS) device (e.g., a thermal desorption (TD) GC-MS device).

In some embodiments, the total amount of the moisture or water content can be at most about 500 ppm (e.g., at most about 300 ppm, at most about 200 ppm, at most about 100 ppm, at most about 50 ppm) and/or at least about 10 ppm (e.g., at least about 50 ppm, at least about 100 ppm, or at least about 150 ppm) of the purified organic solvent. In some embodiments, the purified organic solvent is free of water. The moisture or water content in the solvent described herein can be measured by using a Volumetric or Coulometric Karl Fisher titrator.

FIG. 1 is a schematic diagram showing a configuration of a purification system according to some embodiments of the present disclosure. As shown in FIG. 1, the purification system 100 includes raw material feed container 1, first filter unit 2, raw material tank 3, pump 4, pre-heater 5, first distillation column 6, condenser 6a, reboiler 6b, pump 7, second distillation column 8, condenser 8a, reboiler 8b, distilled solvent tank 9, pump 10, heat exchanger 11, second filter unit 12a, third filter unit 12b, and product container 13, all of which are in fluid communication with each other (e.g., through one or more pipes or conduits). In purification system 100, distilled solvent tank 9, pump 10, heat exchanger 11, second filter unit 12a, and third filter unit 12b can be optional and can be in fluid connection with one another through an optional recirculation conduit 150 to form a recirculation loop. In general, purification system 100 can include other components (such as pumps, temperature control units, supply ports, outflow ports, or valves) that may not be shown in FIG. 1.

In general, raw material feed container 1 is configured to hold or transport a starting material (e.g., a pre-processed or unpurified organic solvent). The starting material can be processed by purification system 100 to produce or manufacture a purified organic solvent in which the number of unwanted contaminants (e.g., particulates, organic impurities, metallic impurities, and moisture) are limited within predetermined ranges. The type of raw material feed container 1 is not particularly limited as long as it continuously or intermittently supplies the starting material to the other components of purification system 100. In some embodiments, raw material feed container 1 can be a tank, such as a stationary tank or a mobile tank. In some embodiments, raw material feed container 1 can include a material receiving tank, a sensor such as a level gauge (not shown), a pump (not shown), and/or a valve (not shown) for controlling the flow of the starting material (not shown).

Purification system 100 can include at least one (e.g., two or three) pre-distillation filter unit and at least one (e.g., two or three) post-distillation filter unit. In general, the pre-distillation filter unit performs an initial filtration of the starting material (e.g., unpurified organic solvent) to remove large particles before distillation, and the post-distillation filter unit performs a filtration after distillation to remove any remaining impurities (e.g., metal or organic impurities) and fine particles to obtain a ultra-high purity organic solvent. In some embodiments, each of the pre-distillation and post-distillation filter units can include a filter housing and one or more filters (e.g., 1-20 filters)) in the filter housing. For example, purification system 100 shown in FIG. 1 includes one pre-distillation filter unit (i.e., first filter unit 2), and two post-distillation filter units (i.e., second filter unit 12a and third filter unit 12b). Distillation columns 6 and 8 shown in FIG. 1 are generally used to remove the majority of the organic and metal impurities and particles.

In some embodiments, each filter unit in purification system 100 can include a filter housing and one or more (e.g., 2, 3, 4, 5, 6, or 7) filters in the filter housing. Each filter can include a filtration medium made from a suitable material and having an appropriate average pore size. The filters can be arranged in parallel or in series in the filter housing. During use, when two filters are arranged in parallel in a filter housing, a solvent to be purified passes these two filters in parallel (i.e., substantially at the same time). On the other hand, when two filters are arranged in series, a solvent to be purified passes these two filters sequentially during use. In some embodiments, some filter units can include a plurality of filters in parallel in the filter housing to increase overall flow rate and improve capacity.

For example, purification system 100 shown in FIG. 1 includes three filter units (i.e., units 2, 6, and 8), each of which includes a filter housing and one or more filters in the filter housing. In other embodiments, purification system 100 can also include other purification modules in addition to the three filter units shown in FIG. 1.

Referring to FIG. 1, filter units 2, 6, and 8 can be different in functionality or property and offer different purification treatments. In some embodiments, each filter unit can independently be selected from the group consisting of a particle removal filter, an ion exchange filter, and an ion absorption filter. In some embodiments, the filters accommodated within each of filter units 2, 6, and 8 can have the same or similar purification function, physiochemical properties, pore size and/or construction material.

In some embodiments, purification system 100 can include at least one (e.g., two or three) first filter unit 2 between raw material feed container 1 and first distillation column 6 and in fluid communication with container 1 and column 6. First filter unit 2 can include a filter housing and at least one (e.g., 2, 3, 4, or 5) filter in the filter housing. In some embodiments, when first filter unit 2 includes two or more filters, these filters can be arranged in parallel to improve flow rate and capacity.

In some embodiments, the filters in first filter unit 2 can be a particle removal filter to remove relatively large particles from the organic solvent. In some embodiments, the filters in first filter unit 2 can include a filtration medium having an average pore size of at most about 0.25 μm or 250 nm (e.g., at most about 240 nm, at most about 220 nm, at most about 200 nm, at most about 180 nm, at most about 160 nm, or at most about 150 nm) and/or at least about 0.05 μm or 50 nm (e.g., at least about 60 nm, at least about 70 nm, at least about 80 nm, at least about 90 nm, at least about 100 nm, at least about 110 nm, at least about 120 nm, at least about 130 nm, at least about 140 nm, or at least about 150 nm). Within the above range, it is possible to reliably remove foreign matters such as impurities or aggregates contained in the organic solvent while suppressing clogging of the filters in first filter unit 2.

Examples of suitable materials of the filtration media in the filters in first filter unit 2 include a fluoropolymer (e.g., polytetrafluoroethylene (PTFE), perfluoroalkoxy alkane polymers (PFA), or a modified polytetrafluoroethylene (MPTFE)), a polyamide such as nylon (e.g., nylon 6 or nylon 66), a polyolefin (including high density and ultrahigh molecular weight resins) such as polyethylene (PE) and polypropylene (PP), or a copolymer thereof. For example, the filtration medium in a particle removal filter can be made of at least one polymer selected from the group consisting of polypropylene (e.g., high density polypropylene), polyethylene (e.g., high density polyethylene (HDPE), or ultra high molecular weight polyethylene (UPE)), nylon, polytetrafluoroethylene, or a perfluoroalkoxy alkane polymer. A filter made of the above materials can effectively remove foreign matters (e.g., those having high polarity) which are likely to cause residue defects and/or particle defects, and to efficiently reduce the content of the metal components in the organic solvent.

In some embodiments, first filter unit 2 can include two, three, or four filters that are arranged in series, have an average pore size of about 50-200 nm, and include a filtration medium made from polypropylene or polytetrafluoroethylene.

Without wishing to be bound by theory, it is believed that using one or more filters having an average pore size of about 50 nm and including a filtration medium made from polytetrafluoroethylene can significant reduce the on-wafer metal count and on-wafer particle of the purified solvent described herein. Without wishing to be bound by theory, it is believed that a filter including a filtration medium made from a fluoropolymer (e.g., polytetrafluoroethylene) can produce less on-wafer particles than a filter including a filtration medium made from a polyolefin (e.g., polypropylene).

In some embodiments, purification system 10 can optionally include raw material tank 3 between and in fluid communication with first filter unit 2 and first distillation column 6. The type of raw material tank 3 is not particularly limited as long as it can hold the solvent filtered by first filter unit 2. Without wishing to be bound by theory, it is believed that raw material tank 3 can provide a sufficient supply of the raw material (e.g., the solvent) for the rest of the purification process and to keep the purification as a continuous process.

In some embodiments, purification system 100 can include a pump 4 and a pre-heater 5 between and in fluid communication with raw material tank 3 and first distillation column 6. During use, pump 4 can deliver the solvent in raw material tank 3 to pre-heater 5 to be heated to a predetermined temperature and then to first distillation column 6. As used herein, pump 4 can be any suitable pump for transporting or delivering a liquid at operating temperature, such as a metering or diaphragm pump.

In general, pre-heater 5 can be any suitable heating device. Examples of pre-heater include a heat exchanger, an electrical heater, a steam heater, or a mineral oil based heater. In general, pre-heater 5 can heat up the organic solvent to a desirable temperature. In some embodiments, pre-heater 5 can heat up the organic solvent to a temperature of from at least about 20° C. (e.g., at least about 19° C., at least about 18° C., at least about 17° C., at least about 16° C., or at most about 15° C.) to at most about 10° C. (e.g., at most about 11° C., at most about 12° C., at most about 13° C., at most about 14° C., or at most about 15° C.) below the boiling point of the organic solvent. For example, when the organic solvent to be purified is cyclohexanone (which has a boiling point of 155.6° C.), pre-heater 5 can heat up the organic solvent to a temperature of at least about 135° C. (e.g., at least about 136° C., at least about 137° C., at least about 138° C., at least about 139° C., or at least about 140° C.) to at most about 145° C. (e.g., at most about 144° C., at most about 143° C., at most about 142° C., at most about 141° C., or at most about 140° C.). Without wishing to be bound by theory, it is believed that pre-heating the organic solvent to the above temperature can facilitate removal of low boiling organic impurities from first distillation column 6, allow the purification process to run continuously, and improve the efficiency and productivity of the purification process. Further, without wishing to be bound by theory, it is believed that, if the organic solvent is pre-heated to a temperature that is too high (e.g., within 10° C. below its boiling point), it can result in temperature overshooting and damaged equipment (e.g., damaged heating element in heat exchanger), reduced product yield (e.g., a certain amount of the organic solvent can be removed with low boiling organic impurities by distillation from the top of first distillation column 6), and an unstable continuous purification process. On the other hand, without wishing to be bound by theory, it is believed that, if the organic solvent is pre-heated to a temperature that is too low (e.g., more than 20° C. below its boiling point), the organic solvent entering first distillation column 6 can be too cold and disrupt the continuing distillation process, which would reduce the overall efficiency of the purification process.

In some embodiments, purification system 100 includes at least two (e.g., three or four) distillation columns. For example, as shown in FIG. 1, purification system 100 includes first distillation column 6 and second distillation column 8, which are downstream of and in fluid communication with pre-heater 5. In general, distillation columns 6 and 8 can be used to purify the organic solvent by distillation to remove the majority of the organic and metal impurities and particles. In some embodiments, first distillation column 6 can be used to remove impurities having a boiling point lower than the boiling point of the organic solvent. In some embodiments, second distillation column 8 can be used to remove impurities having a boiling point higher than the boiling point of the organic solvent, as well as metal impurities and particles that generally cannot be distilled off. Without wishing to be bound by theory, it is believed that switching the order of first distillation column 6 and second distillation column 8 would result in reduced performance, including increased amount of trace metal, increased on-wafer metal count, and increased on-wafer particle count.

In some embodiments, first distillation column 6 can include an inlet for receiving the organic solvent from pre-heater 5 and a first outlet for delivering the organic solvent to second distillation column 8. In general, the inlet is positioned at a location slightly above the packing material in first distillation column 6, where the separation between the low boiling organic impurities and the organic solvent to be purified occurs. In some embodiments, the inlet can be positioned at a location that is from at least about 80% (e.g., at least about 82%, at least about 84%, at least about 86%, at least about 88%, or at least about 90%) to at most about 100% (e.g., at most about 98%, at most about 96%, at most about 94%, at most about 92%, or at most about 90%)

of the height of the first distillation column. Without wishing to be bound by theory, it is believed that placing the inlet at the above location can facilitate the removal of low boiling organic impurities from first distillation column 6, minimize energy required to remove such impurities, and increase the efficiency of the purification process. In general, the first outlet can be located at the bottom of the reboiler 6b of first distillation column 6.

As shown in FIG. 1, first distillation column 6 includes a condenser 6a at the top and a reboiler 6b at the bottom. Condenser 6a can cool or condense the low boiling organic impurities exiting a second outlet of first distillation column 6 to form a liquid, which can then be transferred to a waste container. Examples of condenser 6a include water-cooled condensers (such as tube-and-coil, double tube, or tube-and-shell condensers) and air-cooled condensers. Reboiler 6b can provide heat to the organic solvent to be purified in distillation column 6 to remove impurities having a boiling point lower than the boiling point of the organic solvent from the top of distillation column 6 and can heat the partially purified organic solvent to a suitable temperature (e.g., ±2° C. of the boiling point of the organic solvent) before the solvent is transferred to second distillation column 8 to improve the efficiency and productivity of the purification process. Examples of reboiler 6b include an electrical heater, a steam heater, or a mineral oil based heater.

During operation, upon entering first distillation column 6 through the inlet, the low boiling organic impurities can be distilled off from the top of column 6 through a second outlet for delivering the low boiling organic impurities, cooled by condenser 6a to form a liquid, and transferred to a waste container (not shown in FIG. 1). Because the organic solvent has been pre-heated to a relatively high temperature, the low boiling organic impurities can be distilled off without using a packing material to separate them from the organic solvent to be purified, thereby reducing the energy needed for the distillation and the associated cost. The organic solvent to be purified can be collected at the bottom of first distillation column 6 as an intermediate organic solvent and exit column 6 through the first outlet mentioned above at the bottom of the reboiler 6b. The intermediate organic solvent exiting column 6 can be heated by reboiler 6b to a desired temperature and then be delivered to second distillation column 8 through pump 7. Pump 7 can be any high-purity pump with little metal-containing components, such as a diaphragm pump including PTFE on a portion or the entire inner surface of the pump.

In some embodiments, second distillation column 8 can include an inlet for receiving the organic solvent from first distillation column 6 and a first outlet for delivering the distilled organic solvent to product container 13. In general, the inlet is positioned at a location slightly below the packing material in second distillation column 8. In some embodiments, the inlet can be positioned at a location that is from at least about 0% (e.g., at least about 5%, at least about 10%, at least about 15%, at least about 20%, or at least about 25%) to at most about 30% (e.g., at most about 25%, at most about 20%, at most about 15%, at most about 10%, or at most about 10%) of the height of the second distillation column. Without wishing to be bound by theory, it is believed that placing the inlet at the above location can separate the organic solvent from high boiling organic impurities (e.g., those having a boiling point higher than the boiling point of the organic solvent to be purified), metal impurities, and particles through distillation and facilitate removal of these impurities from second distillation column 8. In general, the first outlet can be located at the top of condenser 8a of second distillation column 8 and above the packing material in column 8.

As shown in FIG. 1, second distillation column 8 includes a condenser 8a at the top and a reboiler 8b at the bottom. Condenser 8a can cool or condense the organic solvent to be purified column 6 to form a liquid, which can then be transferred to distilled solvent tank 9. Examples of condenser 8a include water-cooled condensers (such as tube-and-coil, double tube, or tube-and-shell condensers) and air-cooled condensers. Reboiler 8b can provide heat to the organic solvent to be purified so that it can be distilled off from the top of distillation column 8 and impurities having a boiling point higher than the boiling point of the organic solvent can be removed from the bottom of distillation column 8. In some embodiments, reboiler 8b maintains the temperature of the organic solvent at ±2° C. of the boiling point of the organic solvent. Examples of reboiler 8b include an electrical heater, a steam heater, or a mineral oil based heater.

During operation, upon entering second distillation column 8 through the inlet, the organic solvent can be separated from high boiling organic impurities, metal impurities, and particles through distillation and collected from the top of column 8 as a distilled organic solvent through the first outlet mentioned above at the top of condenser 8a. The high boiling organic impurities, metal impurities, and particles can be collected from the bottom of column 8 through a second outlet for delivering these impurities to a waste container (not shown in FIG. 1).

In some embodiments, purification system 100 can optionally include at least one (e.g., two or three) distilled solvent tank 9 between second distillation column 8 and optional second filter unit 12a and is in fluid communication with column 8 and unit 12a. In general, distilled solvent tank 9 can be any suitable tank known in the art that can be used to store the distilled organic solvent. In some embodiments, distilled solvent tank 9 can be filled with nitrogen to minimize the moisture and oxidation of the solvent stored in the tank. In some embodiments, during the purification process if the purity level of the distilled organic solvent exiting second distillation column 8 meets the predetermined requirements (e.g., having a purity of at least about 99.99%, a moisture content of at most about 100 ppm, and/or metal impurities in a total amount of at most about 200 ppt), the organic solvent can be transferred to product container 13 without passing through tank 9, filter unit 12a or filter unit 12b. On the other hand, if the distilled organic solvent exiting second distillation column 8 does not meet the predetermined requirements, the organic solvent can first be transferred to distilled solvent tank 9, and then can pass through filter units 12a and/or 12b to remove additional impurities. Similarly, if the purity level of the organic solvent exiting filter units 12a and/or 12b meets the predetermined requirements, the organic solvent can be transferred to product container 13. On the other hand, if the purity level of the purified organic solvent exiting filter units 12a and/or 12b does not meet the predetermined requirements, the organic solvent can then be transferred back to distilled solvent tank 9 through optional recirculation conduit 150 and be purified again by filter units 12a and/or 12b.

In general, distilled solvent tank 9 can be any suitable vessel for storing a chemical liquid. In some embodiments, distilled solvent tank 9 can have a suitable volume. For example, distilled solvent tank 9 can have a volume of at least about 1000 liters (e.g., at least about 2000 liters, at least about 3000 liters, or at least about 5000 liters) and/or at most about 30,000 liters (e.g., at most about 25,000 liters, at most about 20,000 liters, at most about 15,000 liters, or at most about 10,000 liters).

In some embodiments, when the distilled organic solvent needs further purification, it can be delivered from distilled solvent tank 9 to second filter unit 12a through pump 10 and heat exchanger 11. Pump 10 can be any pump that can perform recirculation through the tank and filters, such as electromagnetic or centrifuge pumps. In general, heat exchanger 11 can be used to control the temperature of the organic solvent during the subsequent filtration process. Without wishing to be bound by theory, it is believed that if the filtration temperature is too high, the filtration process can generate side reactions, thereby increase the amount of impurities in the solvent. Further, without wishing to be bound by theory, if the filtration temperature is too low, the solvent can have an increased viscosity, which can result in a reduced flow rate. In some embodiments, heat exchanger 11 can control the filtration temperature to from about 10° C. to about 20° C. to avoid underperformance or avoid side reactions.

In some embodiments, purification system 100 can optionally include at least one (e.g., two or three) second filter unit 12a between distilled solvent tank 9 and third filter unit 12b and in fluid communication with tank 9 and unit 12b. In some embodiments, second filter unit 12a can include a filter housing and at least one (e.g., 2, 3, 4, 5, 6, or 7) filters in the filter housing. The filters in second filter unit 12a can be a particle removal filter to remove relative small particles from the organic solvent. In some embodiments, the filters in second filter unit 12a can include a filtration medium having an average pore size of at most about 10 nm (e.g., at most about 9 nm, at most about 8 nm, at most about 7 nm, at most about 6 nm, at most about 5 nm, or at most about 4 nm) and/or at least about 2 nm (e.g., at least about 3 nm, at least about 4 nm, at least about 5 nm, at least about 6 nm, at least about 7 nm, or at least about 8 nm). In some embodiments, the average pore size of the filtration medium in the filters in second filter unit 12a can be smaller than the average pore size of the filtration medium in the filters in first filter unit 2. In such embodiments, second filter unit 12a can be used to remove particles smaller than those removed by first filter unit 2.

Examples of suitable materials of the filtration media in the filters in second filter unit 12a include a fluoropolymer (e.g., polytetrafluoroethylene (PTFE), perfluoroalkoxy alkane polymers (PFA), or a modified polytetrafluoroethylene (MPTFE)), a polyamide such as nylon (e.g., nylon 6 or nylon 66), a polyolefin (including high density and ultrahigh molecular weight resins) such as polyethylene (PE) and polypropylene (PP), or a copolymer thereof. For example, the filtration medium in a particle removal filter can be made of at least one polymer selected from the group consisting of polypropylene (e.g., high density polypropylene), polyethylene (e.g., high density polyethylene (HDPE), or ultra high molecular weight polyethylene (UPE)), nylon, polytetrafluoroethylene, or a perfluoroalkoxy alkane polymer.

In some embodiments, second filter unit 12a can include three to seven filters that are arranged in series, have an average pore size of about 5 nm, and include a filtration medium made from nylon.

In some embodiments, purification system 100 can optionally include at least one (e.g., two or three) third filter unit 12b between second filter unit 12a and product container 13 (i.e., downstream of unit 12b), and in fluid communication with unit 12a and container 13. In some embodiments, third filter unit 12b can include a filter housing and at least one (e.g., 2, 3, 4, or 5) filters in the filter housing. The filters in third filter unit 12b can be a particle removal filter to remove relative small particles from the organic solvent. In some embodiments, the filters in third filter unit 12b can include a filtration medium having an average pore size of at most about 10 nm (e.g., at most about 9 nm, at most about 8 nm, at most about 7 nm, at most about 6 nm, at most about 5 nm, or at most about 4 nm) and/or at least about 2 nm (e.g., at least about 3 nm, at least about 4 nm, at least about 5 nm, at least about 6 nm, at least about 7 nm, or at least about 8 nm). In some embodiments, the average pore size or the filtration medium in the filters in third filter unit 12b can be different from the average pore size or the filtration medium in the filters in second filter unit 12a. In such embodiments, third filter unit 12b can be used to remove particles having a different size or nature from those removed by second filter unit 12a. For example, when second filter unit 12a includes filters having a filtration medium made by nylon, third filter unit 12b can include filters having a filtration medium made by PTFE. Without wishing to be bound by theory, it is believed that nylon filters involve a non-sieving mechanism that can remove metal particles, while PTFE filters involve a sieving mechanism that can remove particles based on pore size.

Examples of suitable materials of the filtration media in the filters in third filter unit 12b include a fluoropolymer (e.g., polytetrafluoroethylene (PTFE), perfluoroalkoxy alkane polymers (PFA), or a modified polytetrafluoroethylene (MPTFE)), a polyamide such as nylon (e.g., nylon 6 or nylon 66), a polyolefin (including high density and ultrahigh molecular weight resins) such as polyethylene (PE) and polypropylene (PP), or a copolymer thereof. For example, the filtration medium in a particle removal filter can be made of at least one polymer selected from the group consisting of polypropylene (e.g., high density polypropylene), polyethylene (e.g., high density polyethylene (HDPE), or ultra high molecular weight polyethylene (UPE)), nylon, polytetrafluoroethylene, or a perfluoroalkoxy alkane polymer. A filter made of the above material can effectively remove foreign matters (e.g., those having high polarity) which are likely to cause residue defects and/or particle defects, and to efficiently reduce the content of the metal components in the organic solvent.

In some embodiments, third filter unit 12b can include two to five filters that are arranged in series, have an average pore size of about 5 nm, and are made from polytetrafluoroethylene.

In some embodiments, purification system 100 can optionally include a recirculation conduit 150 to form a recirculation loop (which can include distilled solvent tank 9, pump 10, heat exchanger 11, and filter units 12a and 12b) for recirculating a partially-purified organic solvent back to distilled solvent tank 9, which can be purified by filter units 12a and/or 12b again. In some embodiments, the partially-purified organic solvent can be recirculated through the recirculation loop at least two times (e.g., at least three times, at least four times, or at least five times) before the organic solvent is transferred to product container 13.

In some embodiments, product container 13 can be a mobile storage tank (e.g., a tank on a tanker) or a fixed storage tank. In some embodiments, product container 13 can be a fluoropolymer lined equipment (e.g., the inner surface of which can include a fluoropolymer such as a PTFE). In some embodiments, product container 13 can have a volume of at least about 200 liters (e.g., at least about 300 liters, or at least about 500 liters) and/or at most about 1,500 liters (e.g., at most about 1200 liters, at most about 1000 liters, at most about 900 liters, at most about 800 liters, at most about 700 liters, or at most about 600 liters).

The present disclosure also features methods of purifying a solvent (e.g., an organic solvent such as cyclohexanone). In some embodiments, the purification method can include (1) distilling the organic solvent in a first distillation column (e.g., first distillation column 6) to obtain an intermediate organic solvent, where the first distillation column has an inlet positioned at a location that is from about 80% to about 100% of the height of the first distillation column; (2) transferring the intermediate organic solvent to a second distillation column (e.g., second distillation column 8), where the second distillation column has an inlet positioned at a location that is from about 0% to about 30% of the height of the second distillation column; and (3) distilling the intermediate organic solvent in the second distillation column to obtain a distilled organic solvent.

For example, referring to FIG. 1, an unpurified or pre-processed solvent (i.e., a starting material) can be purified by purification system 100 by passing the solvent from raw material feed container 1 to raw material tank 3 through first filter unit 2 (in which the solvent is pre-filtered). The solvent can then transferred by pump 4 to preheater 5, in which the solvent is preheated to a temperature of at least 20° C. from the boiling point of the solvent. After pre-heating, the solvent can be transferred to first distillation column 6 to remove low boiling organic impurities and then transferred to second distillation column 8 to remove high boiling organic impurities, metal impurities, and particles. If the distilled solvent exiting second distillation column 8 needs to be further purified, it can be delivered to distilled solvent tank 9 and then to filter units 12a and/or 12b through pump 10 and heat exchanger 11. If the solvent filtered by filter units 12a and/or 12b needs to be further purified, it can be recirculated to distilled solvent tank 9 through recirculation conduit 150 and then be filtered again by filter units 12a and/or 12b.

When the number of particles and the amount of impurities detected from the purified solvent at the end of the purification process are controlled within predetermined ranges, an ultra-high purity solvent (e.g., having a purity of at least about 99.99%, a moisture content of at most about 100 ppm, and/or metal impurities in a total amount of at most about 200 ppt) is produced. Subsequently, the ultra-high purity solvent can be transferred to either product container 13 for storage or to a manufacturing process for making a semiconductor article.

In some embodiments, the solvent purified by the methods and systems described herein can form a film or coating having an on-wafer particle count of at most about 500 (e.g., at most about 450, at most about 400, at most about 350, at most about 300, at most about 250, at most about 200, at most about 150, at most about 100, at most about 50 or at most about 25) or 0 (e.g., at least about 1, at least about 2, or at least about 5) on an entire wafer (e.g., a 12-inch wafer). In some embodiments, the solvent purified by the methods and systems described herein can form a film or coating having an on-wafer metal count (e.g., either a total on-wafer metal count or an on-wafer metal count of a specific metal such as Fe or Ni) of at most about 100 (e.g., at most about 90, at most about 80, at most about 70, at most about 60, at most about 50, at most about 40, at most about 30, at most about 20, or at most about 10, at most about 5) or 0 (e.g., at least about 1 or at least about 2) on an entire wafer (e.g., a 12-inch wafer). In some embodiments, the solvent purified by the methods and systems described herein can form a film or coating having an defect density (i.e., based on the total count of on-wafer metal and particles) of at most about 0.8 (e.g., at most about 0.7, at most about 0.6, at most about 0.5, at most about 0.4, at most about 0.3, at most about 0.2, at most about 0.1, at most about 0.07, at most about 0.05, at most about 0.03, at most about 0.02, at most about 0.01, at most about 0.007, at most about 0.005, at most about 0.004, at most about 0.003) or 0 (e.g., at least about 0.001, at least about 0.01, or at least about 0.1) per square centimeter on an entire wafer (e.g., a 12-inch wafer).

In some embodiments, the methods described herein can be either a continuous process or a batch process. When the methods described herein are a continuous process, the solvent can be purified at a relatively high flow rate. For example, the solvent can be purified at a flow rate of at least about 0.2 L/min (e.g., at least about 0.3 L/min, at least about 0.4 L/min, or at least about 0.5 L/min) and/or at most about 1 L/min (e.g., at most about 0.9 L/min, at most about 0.8 L/min, at most about 0.7 L/min, or at most about 0.6 L/min) through purification system 10. In general, the flow rate for purifying a solvent can vary depending on a number of factors, including the nature and viscosity of the solvent to be purified, the temperature, the number of the filters (e.g., those arranged in parallel), the type and number of other equipment used in the purification process.

The present disclosure is illustrated in more detail with reference to the following examples, which are for illustrative purposes and should not be construed as limiting the scope of the present disclosure.

EXAMPLES

General Description of OWPC and OWMC Measurements

A solvent sample was collected and then inserted into a wafer coating tool. After a bare wafer was coated with a sample, the wafer was transferred to and inspected by a laser-based inspection system. By using a laser light, the laser-based inspection system detected, counted, recorded the location and sizes each particle on the wafer, at a detection limit of 19 nm. More specifically, counting targets included particles having a size of 19 nm or greater. The data was used to create wafer maps and provide the total on-wafer particle counts (OWPC).

The wafer was then transferred to be inspected by EDX (energy dispersive x-ray). Each particle reported by the laser-based inspection system was inspected by EDX (energy dispersive x-ray) for providing the elemental information. Any particle, which was found to produce any metal signal above a threshold calculated from a reference signal, was counted as a metal-containing particle. The total number of particles with a metal signature was totalized to report as OWMP (on-wafer metal particle).

Example 1

Cyclohexanone was the solvent purified in this example. Referring to FIG. 1, cyclohexanone was purified by using the following five purification systems (i.e., Systems 1-5), each of which included at least a pre-filter unit 2 and two distillation filtration systems 6 and 8. The differences among Systems 1-5 are as follows.

In System 1, first distillation column 6, pump 7, and second distillation column 8 were arranged in the following order: column 8, pump 7, and column 6. In addition, System 1 included one 200 nm polypropylene filter (i.e., a filter having a filtration medium made from polypropylene and having an average pore size of 200 nm) in first filter unit 2, but did not include distilled solvent tank 9, pump 10, heat exchanger 11, second filter unit 12a, third filter unit 12b, and recirculation conduit 150.

In System 2, first distillation column 6, pump 7, and second distillation column 8 were arranged in the following order: column 6, pump 7, and column 8. In addition, System 2 included one 200 nm polypropylene filter in first filter unit 2, but did not include distilled solvent tank 9, pump 10, heat exchanger 11, second filter unit 12a, third filter unit 12b, and recirculation conduit 150.

In System 3, first distillation column 6, pump 7, and second distillation column 8 were arranged in the following order: column 6, pump 7, and column 8. In addition, System 3 included one 50 nm PTFE filter (i.e., a filter having a filtration medium made from PTFE and having an average pore size of 50 nm) in first filter unit 2, but did not include distilled solvent tank 9, pump 10, heat exchanger 11, second filter unit 12a, third filter unit 12b, and recirculation conduit 150.

In System 4, first distillation column 6, pump 7, and second distillation column 8 were arranged in the following order: column 6, pump 7, and column 8. In addition, System 4 included one 50 nm PTFE filter in first filter unit 2, distilled solvent tank 9, pump 10, heat exchanger 11, seven 5 nm nylon filters (i.e., filters having a filtration medium made from nylon and having an average pore size of 5 nm) arranged in series in second filter unit 12a, and recirculation conduit 150, but did not include third filter unit 12b. During purification, cyclohexanone was recirculated through the recirculation loop twice (i.e., filtered by filter unit 12a three times).

In System 5, first distillation column 6, pump 7, and second distillation column 8 were arranged in the following order: column 6, pump 7, and column 8. In addition, System 5 included one 50 nm PTFE filter in first filter unit 2, distilled solvent tank 9, pump 10, heat exchanger 11, seven 5 nm nylon filter arranged in series in second filter unit 12a, two 5 nm PTFE filter (i.e., a filter having a filtration medium made from PTFE and having an average pore size of 5 nm) arranged in series in third filter unit 12b, and recirculation conduit 150. During purification, cyclohexanone was recirculated through the recirculation loop twice (i.e., filtered by filter units 12a and 12b three times).

The properties (including on-wafer particle count, total on-wafer metal count, on-wafer iron count, and on-wafer aluminum count) of the cyclohexanone purified by Systems 1-5 described above were evaluated and summarized in Table 1 below.

TABLE 1

| Cyclohexanone | System 1 | System 2 | System 3 | System 4 | System 5 |
| --- | --- | --- | --- | --- | --- |
| On-wafer particle count | >200,000 | 23088 | 639 | 179 | 137 |
| On-wafer metal count (all) | >10,000 | 397 | 9 | 1 | 0 |
| On-wafer metal count (Fe only) | >6,000 | 214 | 7 | 0 | 0 |
| On-wafer metal count (Al only) | >6,000 | 122 | 2 | 1 | 0 |

As shown in Table 1, the cyclohexanone purified by System 1 exhibited saturated high on-wafer particle count, total on-wafer metal count, on-wafer iron count, and on-wafer aluminum count. Surprisingly, the cyclohexanone purified by Systems 2-5 exhibited significantly lower on-wafer particle count, total on-wafer metal count, on-wafer iron count, and on-wafer aluminum count than the cyclohexanone purified by System 1.

More specifically, System 1 differs from System 2 in the order of the two distillation columns. In other words, the cyclohexanone purified by System 1 was first distilled through a distillation column having an inlet at the bottom of the column and then distilled through a distillation column having an inlet at the top of the column. By contrast, the cyclohexanone purified by System 2 was first distilled through a distillation column having an inlet at the top of the column and then distilled through a distillation column having an inlet at the bottom of the column. The results show surprisingly that System 2 can significantly reduce on-wafer particle count, total on-wafer metal count, on-wafer iron count, and on-wafer aluminum count compared to System 1.

In addition, System 3 differs from System 2 by replacing the 200 nm propylene pre-filter in System 2 with a 50 nm PTFE pre-filter. The results show surprisingly that System 3 can significantly reduce on-wafer particle count, total on-wafer metal count, on-wafer iron count, and on-wafer aluminum count compared to System 2.

Further, System 4 differs from System 3 by including a 5 nm nylon filter after the second distillation column. The results show surprisingly that System 4 can significantly reduce on-wafer particle count, total on-wafer metal count, on-wafer iron count, and on-wafer aluminum count compared to System 3.

Lastly, System 5 differs from System 4 by including a 5 nm PTFE filter after the 5 nm nylon filter. The results show surprisingly that System 5 can further reduce on-wafer particle count, total on-wafer metal count, on-wafer iron count, and on-wafer aluminum count compared to System 4.

While the invention has been described in detail with reference to certain embodiments thereof, it will be understood that modifications and variations are within the spirit and scope of that which is described and claimed.

What is claimed is:

1. A method for purifying an organic solvent, comprising:
   distilling the organic solvent in a first distillation column to obtain an intermediate organic solvent, wherein the first distillation column has an inlet positioned at a location that is from about 80% to about 100% of the height of the first distillation column;
   transferring the intermediate organic solvent to a second distillation column, wherein the second distillation column has an inlet positioned at a location that is from about 0% to about 30% of the height of the second distillation column; and
   distilling the intermediate organic solvent in the second distillation column to obtain a distilled organic solvent.

2. The method of claim 1, wherein distilling the organic solvent in the first distillation column removes impurities having a boiling point lower than the boiling point of the organic solvent.

3. The method of claim 1, wherein distilling the intermediate organic solvent in the second distillation column removes impurities having a boiling point higher than the boiling point of the organic solvent.

4. The method of claim 1, further comprising preheating the organic solvent to a temperature at least about 20° C. below the boiling point of the organic solvent before distilling the organic solvent in the first distillation column, wherein the preheating is performed by a preheater upstream of and in fluid communication with the first distillation column.

5. The method of claim 1, further comprising passing the organic solvent through a first filter unit upstream of the first distillation column, wherein the first filter unit comprises a first housing and at least one first filter in the first housing, and the at least one first filter comprises a filtration medium.

6. The method of claim 5, wherein the filtration medium in the at least one first filter comprises a polyolefin, a polyamide, a fluoropolymer, or a copolymer thereof.

7. The method of claim 6, wherein the filtration medium in the at least one first filter comprises polypropylene or polytetrafluoroethylene.

8. The method of claim 5, wherein the filtration medium in the at least one first filter has an average pore size from about 50 nm to about 250 nm.

9. The method of claim 5, wherein the at least one first filter is a particle removal filter.

10. The method of claim 1, further comprising passing the distilled organic solvent through a second filter unit downstream of the second distillation column, wherein the second filter unit comprises a second housing and at least one second filter in the second housing, and the at least one second filter comprises a filtration medium.

11. The method of claim 10, wherein the filtration medium in the at least one second filter comprises a polyolefin, a polyamide, a fluoropolymer, or a copolymer thereof.

12. The method of claim 11, wherein the filtration medium in the at least one second filter comprises nylon or polytetrafluoroethylene.

13. The method of claim 10, wherein the filtration medium in the at least one second filter has an average pore size from about 2 nm to 10 nm.

14. The method of claim 10, wherein the at least one second filter is a particle removal filter.

15. The method of claim 10, further comprising recirculating the organic solvent exiting the second filter unit.

16. The method of claim 15, wherein the recirculating comprises moving the organic solvent exiting the second filter unit to a distilled solvent tank and subsequently passing the organic solvent through the second filter unit, and the distilled solvent tank is between and in fluid communication with the second distillation column and the second filter unit.

17. The method of claim 1, further comprising moving the distilled organic solvent to a product container downstream of and in fluid communication with the second distillation column.

18. The method of claim 1, wherein the organic solvent comprises cyclohexanone, ethyl lactate, n-butyl acetate, propylene glycol monomethyl ether, propylene glycol monomethyl ether acetate, 4-methyl-2-pentanol, or propylene carbonate.

19. A system, comprising:
a first distillation column having a first inlet and a first outlet, wherein the first inlet is positioned at a location that is from about 80% to about 100% of the height of the first distillation column; and
a second distillation column downstream of the first distillation column and having a second inlet and a second outlet, wherein the second inlet is in fluid communication with the first outlet, and the second inlet is positioned at a location that is from about 0% to about 30% of the height of the second distillation column.

20. The system of claim 19, further comprising a preheater, wherein the preheater is upstream of and in fluid communication with the first distillation column.

21. The system of claim 20, further comprising a first filter unit upstream of and in fluid communication with the preheater, wherein the first filter unit comprises a first housing and at least one first filter in the first housing, and the at least one first filter comprises a filtration medium.

22. The system of claim 21, wherein the filtration medium in the at least one first filter comprises a polyolefin, a polyamide, a fluoropolymer, or a copolymer thereof.

23. The system of claim 22, wherein the filtration medium in the at least one first filter comprises polypropylene or polytetrafluoroethylene.

24. The system of claim 21, wherein the filtration medium in the at least one first filter has an average pore size from about 50 nm to about 250 nm.

25. The system of claim 21, wherein the at least one first filter is a particle removal filter.

26. The system of claim 19, further comprising a second filter unit downstream of the second distillation column, wherein the second filter unit comprises a second housing and at least one second filter in the second housing, and the at least one second filter comprises a filtration medium.

27. The system of claim 26, wherein the filtration medium in the at least one second filter comprises a polyolefin, a polyamide, a fluoropolymer, or a copolymer thereof.

28. The system of claim 27, wherein the filtration medium in the at least one second filter comprises nylon or polytetrafluoroethylene.

29. The system of claim 26, wherein the filtration medium in the at least one second filter has an average pore size from about 2 nm to 10 nm.

30. The system of claim 26, wherein the at least one second filter is a particle removal filter.

31. The system of claim 19, further comprising a distilled solvent tank between and in fluid communication with the second distillation column and the second filter unit.

32. The system of claim 31, further comprising a recirculation loop, wherein the recirculation loop comprises the second filter unit and the distilled solvent tank.

33. The system of claim 19, further comprising a product container downstream of and in fluid communication with the second distillation column.

* * * * *